(12) United States Patent
Baumgardner et al.

(10) Patent No.: US 9,222,873 B2
(45) Date of Patent: Dec. 29, 2015

(54) OPTICAL PARTICLE DETECTOR

(71) Applicant: Droplet Measurement Technologies, Boulder, CO (US)

(72) Inventors: Darrel Baumgardner, Boulder, CO (US); Roy Newton, Black Hawk, CO (US)

(73) Assignee: Droplet Measurement Technologies, Inc., Boulder ( * ) Notice: Subject to any disclaimer, the term of this patent is extended or adjusted under 35 U.S.C. 154(b) by 68 days.

(21) Appl. No.: 14/059,165

(22) Filed: Oct. 21, 2013

(65) Prior Publication Data

US 2014/0330459 A1 Nov. 6, 2014

Related U.S. Application Data

(60) Provisional application No. 61/818,837, filed on May 2, 2013.

(51) Int. Cl.
*G01N 21/00* (2006.01)
*G01S 17/95* (2006.01)
*G01S 7/48* (2006.01)
*G01S 7/499* (2006.01)

(52) U.S. Cl.
CPC .............. *G01N 21/00* (2013.01); *G01S 7/4802* (2013.01); *G01S 7/499* (2013.01); *G01S 17/95* (2013.01)

(58) Field of Classification Search
CPC ........ G01N 21/39; G01S 17/107; G01S 17/88
USPC ................. 356/436–437, 28, 28.5, 337–338; 702/17–26
See application file for complete search history.

(56) References Cited

U.S. PATENT DOCUMENTS 6,490,530 B1 * 12/2002 Wyatt ................... G01N 1/2202 702/23

* cited by examiner

*Primary Examiner* — Gregory J Toatley
*Assistant Examiner* — Iyabo S Alli
(74) *Attorney, Agent, or Firm* — Lathrop & Gage LLP

(57) ABSTRACT

An optical device mounted on the interior of an aircraft for distinguishing the morphology of individual atmospheric particles, identifying them as water droplets, ice crystals, dust particles or volcanic ash, including a source of collimated, polarized light and providing this information to the flight crew to assist them in making informed decisions on conditions that might impact aircraft performance.

12 Claims, 3 Drawing Sheets

OPTICAL PARTICLE DETECTOR

RELATED APPLICATIONS

This application claims the benefit of priority of U.S. Provisional Application Ser. No. 61/818,837, filed May 2, 2013, which is incorporated herein by reference in its entirety.

BACKGROUND

1. Field of the Invention

The presently disclosed instrumentalities pertain to a hazard warning device for aircraft. In particular, the device provides warnings that may be heeded to mitigate problems of engine roll back and sensor blockage due high ice crystal concentrations, together with problems of erosion and subsequent damage to aircraft surfaces. This protects also engine turbine blades from extended encounters with dust and volcanic ash.

2. Description of the Related Art

High concentrations of airborne particles present a hazard to aviation. These particles, especially water droplets, ice crystals, dust particles or volcanic ash particles, may contribute to such major problems as accidents and loss of life. The particles may also cause costly damage to aircraft parts. Aircraft at this time have no systems for detecting when they are encountering these particles other than visual observations by the flight crew.

Commercial aircraft are equipped with forward looking radar systems for detecting precipitation-sized cloud particles that allow them to avoid regions with hail, lightning and other cloud phenomenon that could be hazardous for flight operations. These radar operate at a wavelength that is sensitive to hydrometeors larger than 100 µm, but cannot detect regions where there are very high ice crystal concentrations since these types of crystals are typically much smaller than 100 µm. Likewise, dust and ash particles are much smaller than 100 µm and cannot be detected by the aircraft weather radar system. Potentially hazardous dust and ash particles are found in thin layers that cannot be observed by the flight crew from below or above and are only visible when looking through them horizontally due to their optical thickness. When these layers are embedded in clouds, they are impossible to discern by eye.

Other than the weather radar, commercial aircraft are equipped with no other sensor capable of measuring the characteristics of cloud, dust and ash particles and hence have no way of recognizing when the aircraft is within potentially hazardous conditions.

SUMMARY

The presently disclosed instrumentalities overcome the problems outlined above and advance the art by providing an optoelectronic device for identifying individual water droplets, ice crystals, dust and volcanic ash particles and that works through an optical window of an aircraft.

According to one embodiment, an optoelectronic device detects and identifies individual particles as water droplets, ice crystals, dust particles and volcanic ash particles. A source of polarized, monochromatic radiation transmits light along an optical pathway to illuminate a sample volume of air external to the aircraft. Individual atmospheric particles pass through the sample volume. The optical pathway passes through a light transmissive window or aperture at the boundary of the aircraft skin. Return signals from scattered or reflected light are processed to provide the particle information. A flight crew report generator that creates an information packet for aircraft flight crews to assist in decision making related to hazard avoidance.

The optical pathway has a number of components. An optical subsystem monitors the clarity of light transmission through the light transmissive window, and may provide an indicator warning if maintenance is required to clear the window. Another optical subsystem collects light scattered from individual particles over an explicit collection angle from 137° to 173°. This collection angle of 137° to 173° is selected by numerical modeling and laboratory testing to optimize the collection of light scattered by individual particles within the illuminated volume of air This angle defines a precise optical volume so that the sample volume of each measurement is well defined and that selectively directs the polarized components of the scattered light to photodetectors respectively allocated to S and P components of the polarization. The photodetectors quantify the intensity and change in polarization state caused by the interaction of each particle with the incident illumination.

Return light from the optical pathway is processed to ascertain information representative of particles exterior to the aircraft. The optical pathway terminates at a signal processor that converts the light into current or voltage and conditions the current pulses from the photodetectors by removing electronic noise, restoring baseline shifts and analyzing the pulse shapes. A signal analyzer then extracts the maximum amplitude, width, rise time and fall time of individual pulses from the S and P detectors. An information synthesizer receives the signals from the signal processors, identifies the particle type, derives the equivalent optical diameter (EOD), creates the particle number and mass size distributions, calculates number and mass concentrations, and sends the data to the online storage system and to the flight crew report generator.

In one aspect, the online storage system may be queried by telemetry or wireless communication links.

In one aspect, the source illumination beam is generated by a diode laser, of fixed wavelength, linear polarization and Gaussian intensity distribution;

In one aspect, the sample volume is further defined by the collection optics including a slit aperture of fixed width, height and angle with respect to the collection optics and the illuminated sample volume. Light scattered by individual particles is collected and directed through the slit aperture to a polarized beam splitter that separates the light into two components: 1) the S component as having an angle of polarization that is parallel to that of the incident laser beam and 2) the P component as one having an angle of polarization that is perpendicular to the incident laser beam. One detector measures only the component of polarized scattered light that is at the same angle of polarization as the incident light, which is hereinafter referred to as the S component. Additionally, the waveforms of the signals from these two detectors that are captured during the passage of the particle through the beam are processed to extract additional information that is relevant with respect to the morphology of the particle. Defining the sensitive area of the illuminated sample volume in this manner for use in detecting the optical characteristics of individual particles within this sample volume facilitates quantitation of particle number and mass size distributions from measurements along the flight path of the aircraft.

In one aspect, the two components of polarized scattered light, which are perpendicular to one another, may be focused on respective avalanche photodetectors that convert the scattered light photons to an electrical current that is processed to remove electronic noise and baseline drifts, analyzed to measure the detailed shape of the signal, more specifically to measure the peak, width, area, rise and fall times and non-Gaussian features of the two polarized components produced by each individual particle detected in the viewing volume.

According to one embodiment, all of the signal shape information produced by the signal processor for the parallel and perpendicular components of the polarized scattered light is synthesized to identify if the particle is a water droplet, ice crystal, dust particle, volcanic ash particle or some other type of atmospheric particle. The synthesizer utilizes a neural network that has been programmed into a field programmable gate array (FPGA). The neural network has been trained using actual water droplets, ice crystals, ash and dust particles, supplemented with additional shapes produced with a numerical model. The synthesizer also derives an equivalent optical diameter and over fixed time intervals generates distributions of number and mass concentration as a function of size. Determination of the optical equivalent diameter and morphological complexity relies on the fact that these two quantities are related to how particles interact with an incident plane wave of electromagnetic radiation. Theoretical calculations to address this may be derived using the Taylor-Maxwell equations with some knowledge also of the particle properties.

These measurements are used to calculate the equivalent optical diameter from which particle volume and mass are estimated. This analysis operates on inputs including the peak S and P intensities, their sum, and the waveform information. The modeling transforms this information into three quantities: 1) the optical equivalent diameter, 2) the morphological complexity, and 3) the classification of the particle as a water droplet, ice crystal, dust particle, volcanic ash or undefined.

Output from the signal processor may be combined into a textual and graphical report that is available to the flight crew for making informed decisions about flight operations that could be affected by the presence of water droplets, ice crystals, dust particles or volcanic ash particles.

The optoelectronic device described herein may be advantageously constructed of very lightweight, low power and small volume components making the size, weight and power consumption small enough for easy mounting and operation on aircraft. In addition, the optoelectronic device may be operated autonomously with no need for operator intervention.

BRIEF DESCRIPTION OF THE DRAWINGS

The invention will be understood more clearly and other advantages shall appear in the following description given on a purely non-restrictive basis with reference to the appended drawings in which.

DETAILED DESCRIPTION OF SYSTEM

Figure 1:
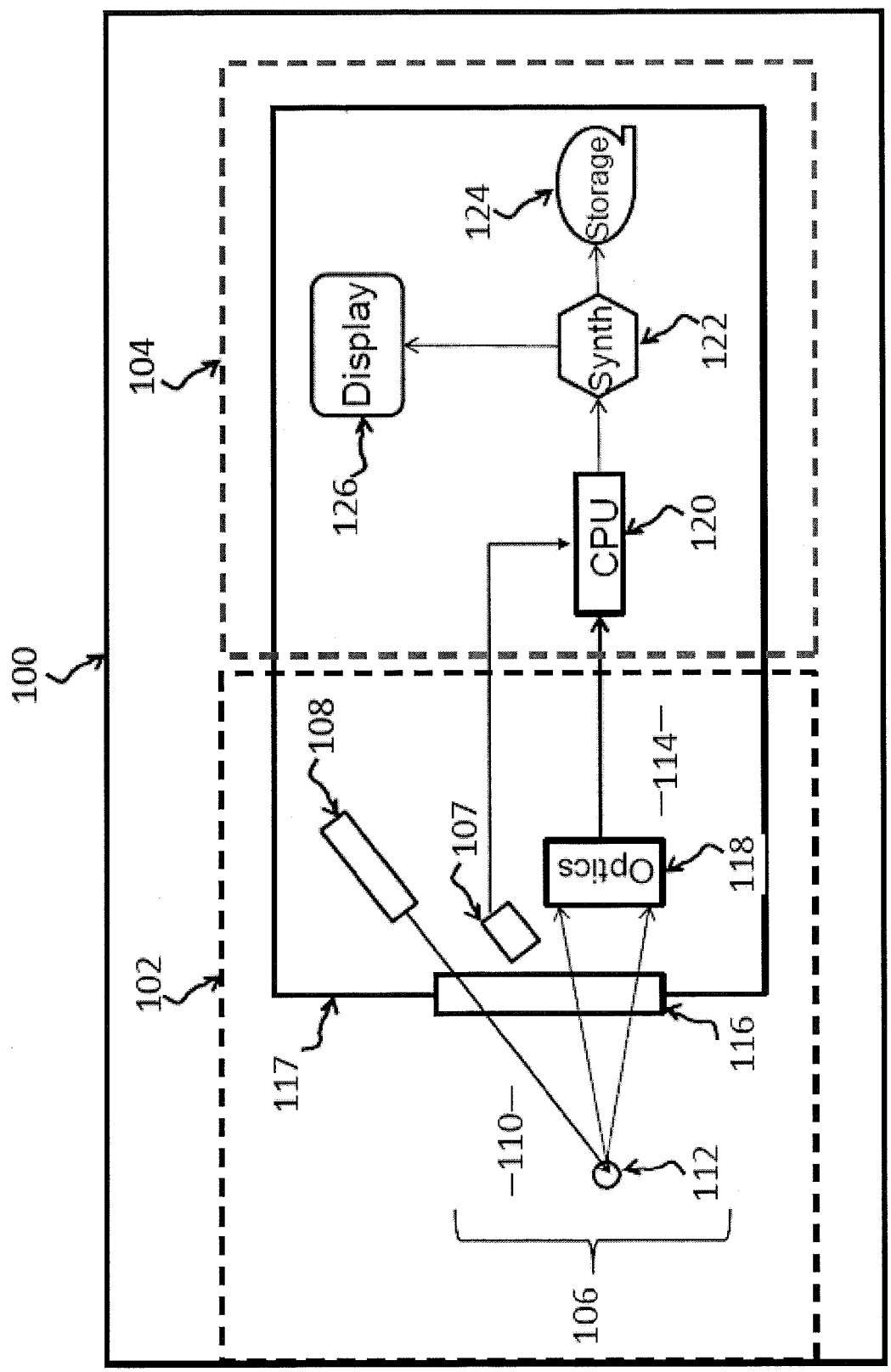
FIG. 1 illustrates the basic components of an optoelectronic device for the detection and identification of individual water droplets, ice crystals, dust particles and volcanic ash particles.

FIG. 1 shows an optoelectronic device 100 for the detection and identification of individual particles including water droplets, ice crystals, dust particles and volcanic ash particles. The optical device 100 includes two subsystems, i.e., a detection system 102 and an information processing and reporting system 104.

The detection system 102 provides an optical pathway 106 for the transmission of light emanating from source 108. Source 108 directs light on pathway 106 into space 110 outside an aircraft and towards a sample volume 112. Light scattered by any individual water droplet, ice crystal, dust particle or volcanic ash particle in the sample volume 112 returns to an instrument interior 114 through a light-transmissive window or transparent aperture 116 in airplane skin 117. The optical pathway 106 terminates into an optical detection block 118. In this manner, the detection system 102 collects the light scattered by an individual water droplet, ice crystal, dust particle or volcanic ash particle in the sample volume 112.

An optical surveillance system 107 views return light from source 108 passing through the transparent aperture 116 and detects light that scatters from any contamination that may reside on the inside or outside of the transparent aperture 116, indicating the need for preventive maintenance.

Figure 2:
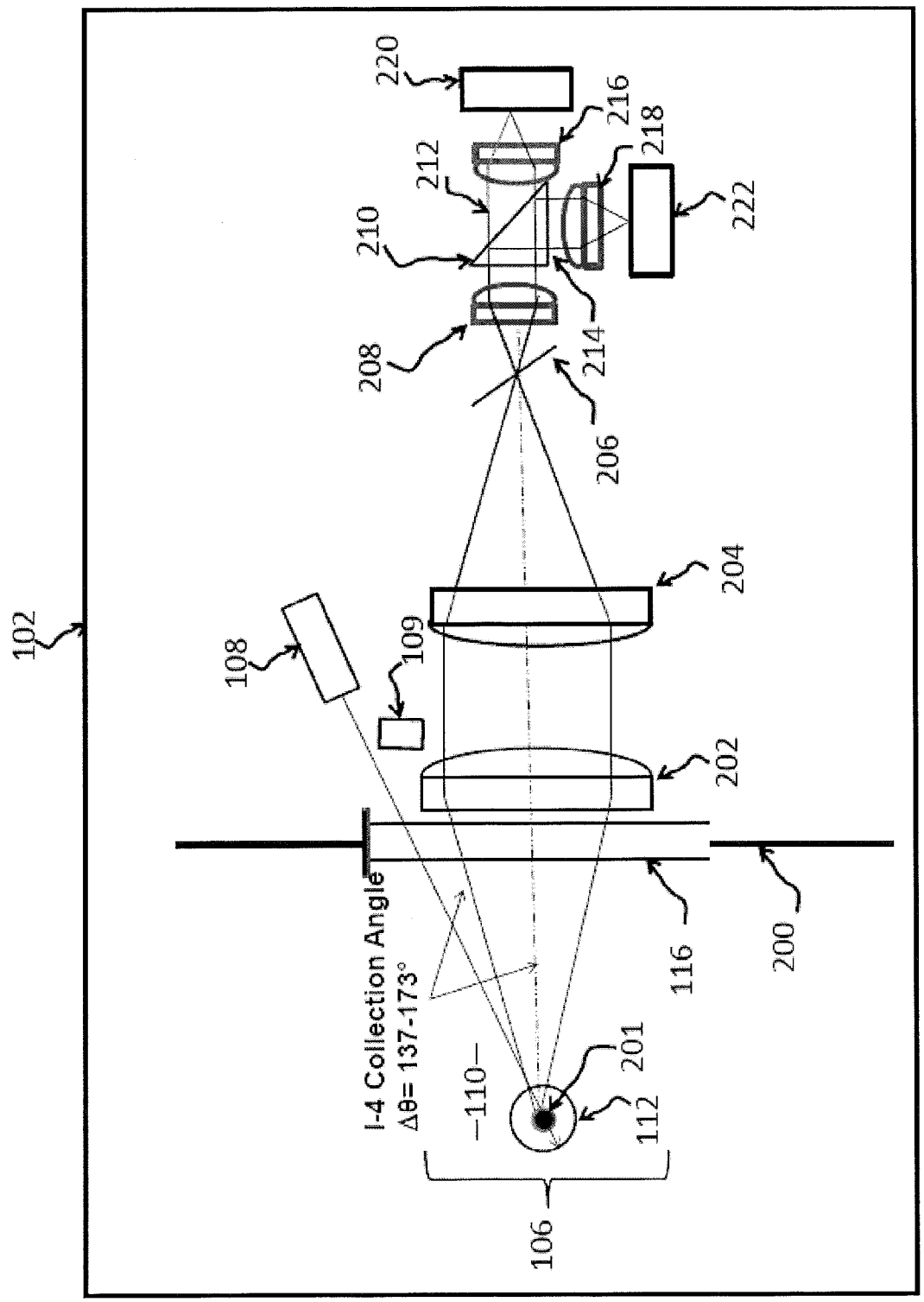
FIG. 2 provides the details of the optical detection system.

When the optical source 108 is a diode laser, for example as shown in FIG. 2 below, the optical system 107 may be for example a photodiode (not shown) with a light filter in front of it that has a bandpass wavelength equal to the wavelength of the diode laser 108. The signal from this photodiode is transmitted to the signal processor 120. The optical detection block 118 converts photons from the optical pathway 106 into electrical signals that are sent to a signal processor 120 where the signals are conditioned and analyzed. The processed signals from signal processor 120 travel to an information synthesizer 122 that identifies the particle size by type of particle, generates information that is stored on a removable recording medium 124 and also sent to flight crew display 126. The information synthesizer 120 also monitors the signal from optical system 107 to determine the transmission efficiency of the transparent aperture 116.

FIG. 2 provides additional detail about detection system 102 according to one embodiment. Here the source 108 is a polarized diode laser directing its beam on pathway 106 through a fused silicate light transmissive window 116 that is mounted in aircraft skin 200, which is optionally heated to eliminate excess moisture. The laser beam on pathway 106 illuminates an individual particle 201 that passes through sample volume 112, which may be a volume of air outside the aircraft.

A configuration of collimating and focusing lenses 202, 204 collect the light scattered by particle 201 over a precise range of angles ranging from 137°-173°. These angles have been selected through optical calculations to produce the optimum intensity of scattered light from each particle 201. The collimating and focusing lenses 202, 204 direct the collected, scattered light on pathway 106 through a slit aperture 206 having an angle, aperture length and width that define the size of the sample volume 112.

A focusing lens 208 directs light to a polarized beam splitter 210 that separates the scattered light into two components 212, 214, each having a polarization that is perpendicular to one another. The respective components 212, 214 are then directed by the corresponding focusing lenses 216, 218 onto the avalanche photo diode (APD) 220, 222, which are detectors that convert the scattered light photons into an electric current. The APDs 220, 222 represent a "P" APD 220 that designates the detector associated with scattered light with polarization parallel to that of the incident laser light and a "S" APD 222 that designates the detector associated with scattered light with polarization perpendicular to that of the incident laser light.

Figure 3:
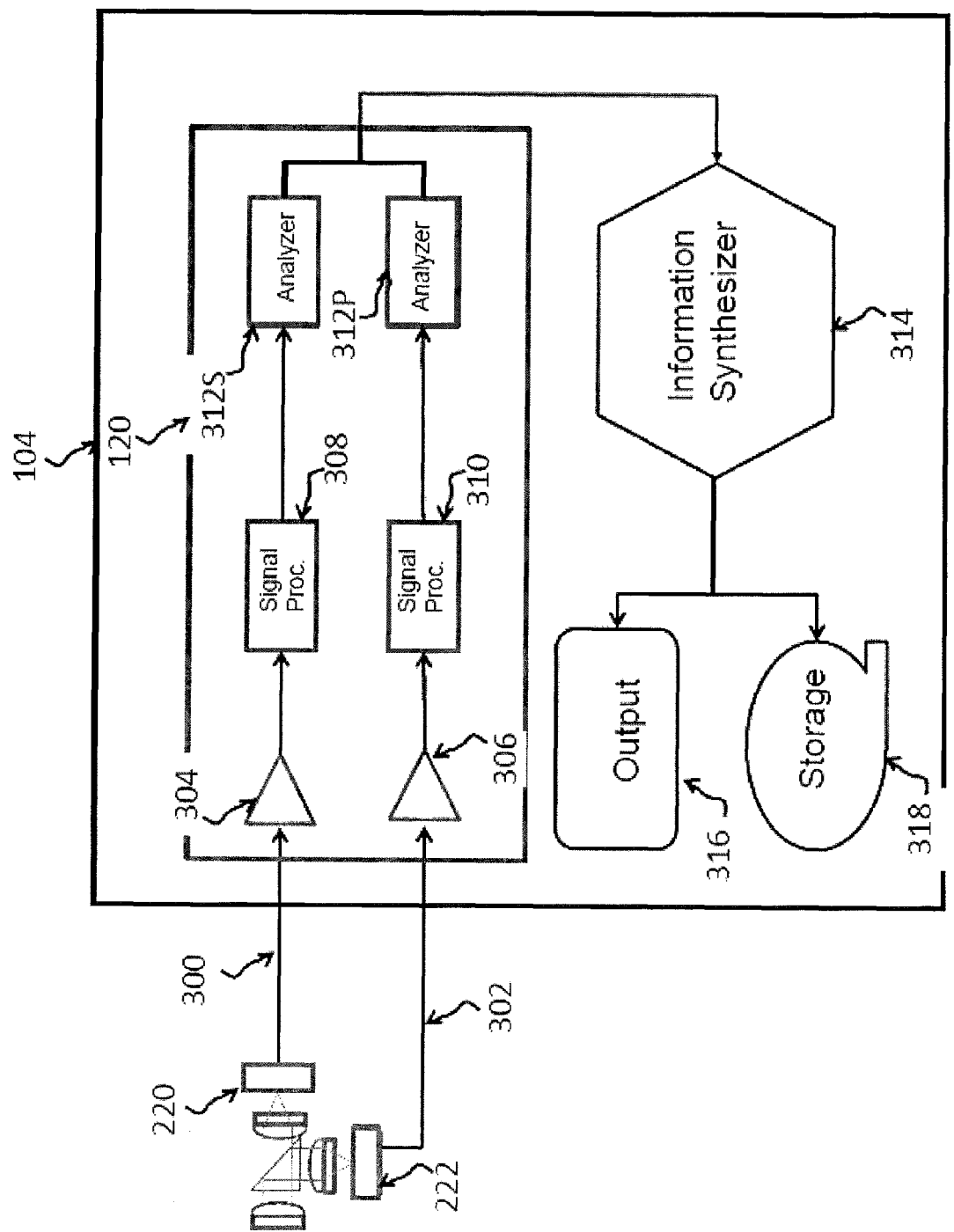
FIG. 3 provides the details of the information processing and reporting system.

FIG. 3 provides additional detail about the information processing and reporting system 104 according to one embodiment. The signal processor 120 receives separate signals 300, 302 from APDs 220, 222. The signal processor 120 converts the signals, such as by converting current to voltage, with amplifiers 304, 306 passing these voltages to signal conditioners 308, 310. The signal conditioners 308, 310 filter electronic noise and remove offsets to restore a signal baseline before passing the signals to shape analyzers 312P, 312S, which extract the peak heights, areas, widths, rise times and decay times for the "P" and "S" signals from each particle.

An information synthesizer 314 is for example, a neural network or multivariate parameter analyzer operating upon the signal shapes, for example, including the respective peak heights, areas, widths, rise times and decay times from the "P" and "S" polarized signals. This input is submitted into a neural network that has been trained using actual atmospheric particles, crystal analogs and model simulations to produce output that identifies the particles by size and type, i.e., water droplets, different shapes of ice crystals, dust particles and volcanic ash particles. In addition, the information synthesizer derives the particle velocity and equivalent optical diameter (EOD) from which the number and mass concentration size distribution is assessed over fixed intervals of time.

Given that the aircraft on which this instrument is operated can travel over a range of velocities, the signal processor 120 and information synthesizer 314 preferably use state of the art high speed analog and digital electronics to digitize pulses that are less than a microsecond in length and a Field Programmable Gate Array (FPGA) to implement the neural network in real-time.

A reporting system 316 that takes the information from information synthesizer 314 and presents the data on particle number, concentration, liquid water concentration, ice water fraction and other parameters as needed by the flight crew to make informed decisions about environmental conditions that might impact the performance of the aircraft.

A data storage system 318 records all the raw data necessary to monitor the sufficiency of the detection and information processing system 100 in addition to the S and P electrical signals that are used to derive particle type and EOD. The data storage system is of high capacity sufficient to record up to one hundred hours of flight and is easily removable for offline data transfer.

The foregoing disclosure teaches by way of example, and not by limitation. Those skilled in the art will appreciate that what is described may be subjected to insubstantial changes without departing from the true scope and spirit of the invention. Accordingly, the inventors hereby state their intention to rely upon the Doctrine of Equivalents if need to protect their full rights to what is claimed.

What is claimed is:

1. An optoelectronic device for detection and identification of individual water droplets, ice crystals, dust particles and volcanic ash particles, the device comprising:
   a source of collimated monochromatic radiation that illuminates an area of air external to the aircraft through which freely pass individual atmospheric particles to create an illuminated sample volume of air;
   an optical surveillance system for monitoring the clarity of light transmission through the light transmissive window to indicate a need for preventive maintenance;
   an optical detection system that is constructed and arranged to collect light scattered from individual particles over an explicit angle ranging from 137° to 173° that defines the illuminated sample volume for measurement of S and P components of return scattered light from the sample volume to photodetectors that provide signals representative of intensity and change in polarization state caused by the interaction of particles with the incident illumination in the sample volume;
   a signal processor that is constructed and arranged to condition the signals from the photodetectors by removing electronic noise, restoring baseline shifts and analyzing the pulse shapes to provide processed signals;
   a signal analyzer configured to operate upon the processed signals for extraction of data representing maximum amplitude, width, rise time and fall time of individual pulses in the S and P components;
   an information synthesizer that receives the data and produces analytical results allocated to particles by particle type including equivalent optical diameter (EOD), number and mass size distributions, and number and mass concentrations,
   the particle type being selected as at least one member among the group consisting of individual water droplets, ice crystals, dust particles and volcanic ash particles;
   a report generator that creates an information packet utilizing information form the information synthesizer to assist in decision making related to hazard avoidance for aircraft flight,
   the optoelectronic system being constructed for mounting and operation on an aircraft.

2. The optoelectronic device, according to claim 1, wherein a diode laser is provided as the source of collimated monochromatic radiation to generate an illumination beam as one having fixed wavelength, linear polarization and Gaussian intensity distribution.

3. The optoelectronic device, according to claim 1, wherein the information synthesizer includes a neural network that is trained to operate upon peak heights, peak areas, widths, rise times and decay times of the S and P components.

4. The optoelectronic device, according to claim 2, wherein the optical detection system includes a slit aperture of fixed width, height and angle with respect to the collection optics and illuminated volume.

5. The optoelectronic device, according to claim 4, wherein the optical detection system is constructed to collect light scattered by individual particles after passing through the slit aperture and direct such light to a polarized beam splitter that separates the light into the S and P components as: 1) one whose angle of polarization is parallel to that of the incident laser beam and 2) one whose angle of polarization is perpendicular to the incident laser beam.

6. The optoelectronic device, according to claim 5, wherein the S and P components are respectively focused on individual, avalanche photodetectors that convert the scattered light photons to an electrical current that is processed to remove electronic noise and baseline drifts, analyzed to measure the detailed shape of the signal, more specifically to measure the peak, width, area, rise and fall times and non-Gaussian features of the two polarized components produced by each individual particle detected in the viewing volume.

7. The optoelectronic device, according to claim 6, wherein the signal analyzer includes a neural network that is implemented through programming of a floating point gated array to assess particle type.

8. The optoelectronic device, according to claim 7, a including a reporting system that presents information from the information synthesizer in a textual and graphical format for facilitating informed decisions about flight operations affected by the presence of water droplets, ice crystals, dust particles or volcanic ash particles.

9. A method of detecting and identifying individual water droplets, ice crystals, dust particles and volcanic ash particles, by use of the device according to claim 1 on an aircraft, the method comprising the steps of:
- illuminating a volume of air external to the aircraft by use of the source of collimated monochromatic radiation
- surveiling the clarity of light transmission by use of the optical surveillance system;
- collecting light scattered from individual particles over the explicit solid angle ranging from 137° to 173° by use of the optical detection system;
- a signal processor that is constructed and arranged to condition the signals from the photodetectors by removing electronic noise, restoring baseline shifts and analyzing the pulse shapes to provide processed signals;
- extracting from the signals the data representing the maximum amplitude, width, rise time and fall time of individual pulses in the S and P components by use of the signal analyzer; and
- producing the analytical results in real time by use of the an information synthesizer.

10. The optoelectronic device of claim 1 wherein the information synthesizer provides the data by particle type for all members of said group.

11. The optoelectronic device of claim 1 wherein the information synthesizer includes a neural network of a nature that is trained utilizing laboratory measurements with water droplets, ice crystals, dust particles and volcanic ash.

12. The optoelectronic device of claim 11 wherein the neural network is also trained utilizing computational results from a numerical model utilizing Taylor-Maxwell equations.

\* \* \* \* \*